United States Patent [19]
Lunn et al.

[11] Patent Number: 5,578,464
[45] Date of Patent: Nov. 26, 1996

[54] E. COLI SECRETORY STRAINS

[75] Inventors: Charles A. Lunn, Bloomfield; Satwant K. Narula, Caldwell; Richard L. Reim, Edison, all of N.J.

[73] Assignee: Schering Corporation, Kenilworth, N.J.

[21] Appl. No.: 438,803

[22] Filed: May 11, 1995

Related U.S. Application Data

[63] Continuation of Ser. No. 818,737, Jan. 7, 1992, abandoned, which is a continuation of Ser. No. 429,588, Oct. 31, 1989, abandoned.

[51] Int. Cl.$^6$ .............................. C12N 1/21; C12N 15/72
[52] U.S. Cl. ................ 435/69.1; 435/172.3; 435/252.33; 435/320.1
[58] Field of Search ............................. 435/69.1, 172.3, 435/252.33, 320.1

[56] References Cited

U.S. PATENT DOCUMENTS

| | | | |
|---|---|---|---|
| 4,336,336 | 6/1982 | Silhavy et al. | 435/172.3 |
| 4,595,658 | 6/1986 | Zinder et al. | 435/69.7 |
| 4,757,013 | 7/1988 | Inouye et al. | 435/172.3 |
| 5,017,691 | 5/1991 | Lee et al. | 535/351 |

FOREIGN PATENT DOCUMENTS

| | | | |
|---|---|---|---|
| 0006694 | 9/1980 | European Pat. Off. | C12P 21/02 |
| 331356 | 9/1989 | European Pat. Off. | |

OTHER PUBLICATIONS

M.G.G. 147:263–269, 1976, Alphen et al. Heptose–deficient Mutants of *E. coli* K–12 Deficient in Up To Three Outer Membrane Proteins.
M.G.G. 146:43–50, 1976, Havekes et al. conjugation Deficient *E. coli* K 12 F–Mutants with Heptose–less Lipopolysaccharide.
Mol. & Gen. Genet. 183:181–186, 1981, Schwartz et al. Altered Transcriptional Termination in a Rifampicin –Resistant Mutant of *E. coli* which Inhibits Growth of T7.
J. of Biochem. 260:2670–2674, 10 Mar. 1985, Takahara et al. The ompA Signal Peptide Directed Secretion of Staphylococcal Nuclease A by Escherichia coli.
Cole et al., Chem. Abstracts 98:102865b (1983).
Lundell et al., J. Ind. Microbiol. 5:215 (1990).
Dialog Info. Services Abstract of Japanese Patent Appl'n JB63237790, File 351, World Patent Index 81–90, Dialog Accession No. 5029529.
EMBO J. vol. 3:2437–2442; 1984, Ghrayeb et al. Secretion cloning vectors in *Escherichia coli*.
Gene 53:31–40, 1987, Focareta et al, Extracellular proteins of *Vibrio cholerae*: molecular cloning, nucleotide sequence and characterization of the deoxyribonuclease (DNase) together with its periplasmic . . .
Science, vol. 222:778–782, 18 Nov. 1983, Young et al. Yeast RNA Polymerase II Genes: Isolation with Antibody Probes.
Anderson et al., J. Bacteriol. 140:351 (1979).
Lazzaroni et al., J. Bacteriol. 145:1351 (1981).
Lopes et al., J. Bacteriol. 109:520 (1972).
Sakaguchi et al., Agric. Biol. Chem. 52:2669 (1988).
Villa–Komaroff et al., Proc. Natl. Acad. Sci. USA 75:3727 (1978).

*Primary Examiner*—John Ulm
*Attorney, Agent, or Firm*—James M. Gould; Norman C. Dulak

[57] ABSTRACT

Strains of *E. coli* are provided which are capable of secreting heterologous recombinant proteins through the outer cell wall and directly into the culture medium. Methods are also provided for making and identifying such strains, and for using them to make heterologous proteins that have high biological activity, without the need for cell disruption.

28 Claims, 4 Drawing Sheets

E. COLI SECRETORY STRAINS

The present application is a continuation application of U.S. application Ser. No. 07/818,737, filed Jan. 7, 1992, now abandoned, which in turn is a continuation of U.S. application Ser. No. 07/429,588, filed Oct. 31, 1989, now abandoned, the benefit of which applications is claimed pursuant to the provisions of 35 U.S.C. §120.

TECHNICAL FIELD

This invention relates to mutant E. coli strains which are transformed with recombinant vectors and capable of secreting heterologous recombinant proteins into the culture medium, and to methods for producing and identifying such strains. The invention also relates to methods for using such transformants to produce heterologous recombinant proteins in correctly folded, biologically active forms.

BACKGROUND OF THE INVENTION

The methods of recombinant DNA technology have enabled the production of relatively large quantities of biologically important polypeptides and proteins. For much of this work, the bacterium Escherichia coli has been employed as a host organism for the expression of recombinant vectors, but the use of this bacterium has significant limitations. Because of their physical structure, E. coli bacteria expressing genes for recombinant polypeptides or proteins must generally be disrupted by physical, chemical or enzymatic means before the recombinant products can be isolated.

E. coli and other gram negative bacteria are characterized by a central cytoplasm, where proteins are synthesized, and a complex cell membrane structure. There is an external membrane, to which a number of lipid-linked oligosaccharides are bound. When pathogenic gram negative bacteria infect an animal, the production of antibodies specific for these surface oligosaccharides can be important in determining the course of the disease.

Interior to the external membrane is the plasma membrane, which is the major permeability barrier of the cell. This membrane contains proteins that allow certain nutrients and other chemicals to pass into and out of the cell, while excluding others.

Between the external membrane and the plasma membrane is the periplasmic space, or periplasm. This region contacts the outer membrane and contains a peptidoglycan, a highly cross-linked wall-like complex of proteins and oligosaccharides that gives rigidity to the cell.

Most proteins synthesized by E. coli remain in the cytoplasm, but some are found in the periplasm. Proteins which are transported from the cytoplasm to the periplasm contain "signal peptides" which are covalently linked by a peptide bond to the amino termini of the proteins and which facilitate transport through the plasma membrane. Examples of some periplasmic proteins in E. coli are β-lactamase, alkaline phosphatase and certain nucleases, peptidases and proteases. The signal peptides of the periplasmic proteins are generally cleaved at some point during the transport process, leaving the "mature" forms of the proteins in the periplasm.

During the production of recombinant proteins using E. coli, the expression products of heterologous or foreign genes generally accumulate in the cytosol. Such proteins often precipitate to form insoluble "inclusion" or "retractile bodies". Recombinant proteins in such bodies are not in their native conformation and are not biologically active [Mitraki et al., Bio/Technology 7:690 (1989)]. To isolate such proteins in a useful form, the bacteria must be disrupted and the proteins in the insoluble fraction must be solubilized using a detergent or a chaotropic agent such as urea or guanidinehydrochloride. Because proteins thus solubilized are not in their native conformations, they must be correctly refolded using relatively complex procedures such as those described by Builder et al. (European Patent Application Publication No. 114 506).

In an effort to use recombinant DNA methods to produce heterologous proteins that do not accumulate in cytoplasmic inclusion bodies, Villa-Komaroff et al. [Proc. Natl. Acad. Sci. USA 75:3727 (1978)] inserted the rat preproinsulin gene into the E. coli β-lactamase gene. As already noted, b-lactamase is a periplasmic enzyme which, in its precursor form, carries a signal peptide. The fusion protein resulting from the expression of the fused β-lactamase/preproinsulin genes was transported to the periplasm by the above-described transport mechanism.

Similarly, Gilbert et al., (European Patent Application Publication No. 006 694) have disclosed the production of genetically engineered fusion proteins by expression of DNA sequences containing a gene encoding a desired foreign protein fused to a DNA sequence encoding a signal peptide of a periplasmic protein.

Exploiting the natural transport processes a bit further, Silhavy et al. (U.S. Pat. No. 4,336,336) have described a method for producing fusion proteins which are transported into the outer membrane of a bacterium. This method entails the fusion of a gene encoding a cytoplasmic bacterial protein with a gene for a non-cytoplasmic carrier protein, thereby producing a fusion protein which is carried to the outer membrane. Silhavy et al. also disclose that this method could be used to insert a foreign gene (e.g., a gene encoding a eukaryotic protein) into the already constructed fusion gene.

In none of the foregoing processes, however, are the desired recombinant proteins transported beyond the outer membranes of the cells. In each case, the cells must still be disrupted to recover the proteins. As a result, myriad bacterial proteins are also released, rendering the isolation of the desired proteins more laborious and complex. Moreover, where the processes yield products fused to bacterial proteins, the products must generally be cleaved to produce the desired protein. This process may be complex and may entail the use of denaturing conditions, making recovery of proteins having full biological activity difficult.

More recently, Sakaguchi et al. [Agric. Biol. Chem. 52:2669 (1988)] have reported fusing a DNA sequence encoding the ompA signal sequence to a gene encoding granulocyte-macrophage colony stimulating factor (GM-CSF) in an E. coli expression vector. After transformation into E. coli HB101 and expression, it was found that some GM-CSF was secreted into the culture medium.

E. coli mutants which leak various periplasmic enzymes into the culture medium have been produced. For example, Lopes et al. [J. Bacteriol. 109:520 (1972)] treated E. coli cells with a mutagen such as nitrosoguanidine to produce "periplasmic leaky" mutants which secreted ribonuclease I, endonuclease I and alkaline phosphatase. Similarly, Anderson et al. [J. Bacteriol. 140:351 (1979)] and Lazzaroni et. al. [J. Bacteriol. 145:1351 (1981)] have used immunoprecipitation or SDS-polyacrylamide gel electrophoresis to detect secreted periplasmic proteins in studies of periplasmic leaky mutants.

The leakiness of such mutants is believed to reflect a deficiency in a normal component(s) of the bacterial outer membrane which increases permeability. None of the leaky mutants were made with the objective of obtaining secretion of recombinant proteins into the culture medium. Instead, their construction appears to have been carried out to investigate the structure and function of the bacterial envelope and the location of various enzymes within the membrane structure.

More recently, Zinder al. (U.S. Pat. No. 4,595,658) have disclosed a method for facilitating the externalization of proteins synthesized in bacteria. This method entails the introduction of all or a portion of gene III of an fl bacteriophage into a plasmid or bacterial chromosome. The fl bacteriophage gene III protein produced by expression of the gene is said to perturb the outer bacterial membrane, resulting in the leakage of periplasmic proteins from the cell.

Zinder et al. further disclose that their leaky mutants can be used to produce genetically engineered fusion proteins by a method in which a gene encoding a desired protein is fused to a DNA sequence encoding a leader capable of transporting the protein to the periplasmic space. Zinder et al., however, provide no teachings of how such fusions could be carried out and no example to show that the method would actually work as hypothesized. All that is actually shown is that the natural β-lactamase of the mutants leaked from the cells into the surrounding medium.

Because improper chain folding and protein denaturation are associated with recombinant proteins maturing within the cytoplasm and do not generally occur with proteins exported out of the cell, there is a need for a reliable way to make and use *E. coli* secretory strains.

SUMMARY OF THE INVENTION

This invention provides *E. coli* bacteria capable of secreting biologically active heterologous gene products into the culture medium, comprising:

(a) an *E. coli* bacterium characterized by resistance to infection by bacteriophage T7 and an ability to secrete substantial amounts of periplasmic proteins into the culture medium, and (b) a recombinant vector comprising a first DNA sequence coding for a signal peptide capable of mediating transport of a protein to the periplasmic space operatively linked to a second DNA sequence coding for a desired heterologous protein, which bacterium is capable of expressing both DNA sequences.

The present invention further provides methods for producing desired heterologous proteins, comprising:

(a) culturing an *E. coli* bacterium capable of secreting biologically active heterologous proteins into the culture medium, comprising
 (i) an *E. coli* bacterium characterized by resistance to infection by bacteriophage T7 and an ability to secrete substantial amounts of periplasmic proteins into the culture medium, and
 (ii) a recombinant vector comprising a first DNA sequence coding for a signal peptide capable of mediating transport of a protein to the periplasmic space operatively linked to a second DNA sequence coding for a desired heterologous protein,
under conditions in which the bacterium expresses both DNA sequences and secretes the heterologous protein into the culture medium; and (b) isolating the secreted protein from the culture medium.

This invention still further provides methods for making and identifying *E. coli* bacteria capable of secreting biologically active heterologous gene products into the culture medium, comprising:

(a) subjecting *E. coli* bacteria to a sufficient amount of a mutagenic agent to produce mutational changes in the DNA of the bacteria;

(b) selecting clones of the mutants produced in step (a) for resistance to infection by bacteriophage T7 and an ability to secrete substantial amounts of periplasmic proteins into the culture medium;

(c) transforming one or more of the clones selected in step (b) with a recombinant vector comprising a first DNA sequence coding for a signal peptide capable of mediating transport of a protein to the periplasmic space operatively linked to a second DNA sequence coding for a desired heterologous protein, which recombinant vector is capable of directing expression of both DNA sequences in the bacteria; and (d) analyzing the transformed clones to determine which clones are secreting substantial amounts of the heterologous protein into the culture medium.

In a preferred embodiment, analysis of the transformed clones is carried out by a method comprising:

(a) contacting a first nitrocellulose membrane with a dispersed culture of the transformed bacteria, under conditions in which a portion of the colonies in the culture is transferred onto one side of the membrane;

(b) contacting the other side of the first membrane of step (a) with a second nitrocellulose membrane in contact with a growth medium, to produce a membrane assembly;

(c) incubating the membrane assembly under conditions in which biologically active protein secreted by the transferred bacteria passes through the first membrane to the second membrane;

(d) separating the membranes and contacting the second membrane of step (c) with a first antibody specific for the protein, under conditions in which specific antibody-protein complexes form;

(e) washing the second membrane of step (d) to remove unbound materials;

(f) contacting the washed membrane with a labeled second antibody specific for the first antibody, under conditions in which a visible reaction occurs where first antibody-protein complexes are present on the membrane, to produce visible foci; and (g) aligning the visible foci with the bacterial colonies in the culture, thereby identifying bacteria capable of secreting substantial amounts of protein into the culture medium.

Preferably, the first antibody specifically binds to the biologically active protein but not to denatured (i.e., improperly folded) forms of the protein.

BRIEF DESCRIPTION OF THE FIGURES

This invention may be more readily understood by reference to the accompanying figures, in which.

DESCRIPTION OF THE INVENTION

Many of the methods of recombinant DNA-technology routinely used by those of skill in the art have been described by Cohen et al. (U.S. Pat. No. 4,237,224), Collins et al. (U.S. Pat. No. 4,304,863) and Maniatis et al. (Molecular Cloning: A Laboratory Manual, 1982, Cold Spring Harbor Laboratory). These and all other references cited herein are hereby incorporated in their entirety by reference.

This invention is based upon the surprising discovery that *E. coli* can be modified to secrete heterologous proteins directly into the culture medium. As used herein, the term "heterologous proteins" means proteins not ordinarily made by *E. coli*, such as mammalian proteins. Because of this invention, the usual requirement for disruption of the cells and/or extraction with detergents or chaotropic agents in the isolation of heterologous proteins is eliminated.

This result has been achieved by two principal developments. Firstly, recombinant DNA methodology has been applied to produce desired heterologous proteins fused to signal peptides which are capable of mediating transport of the protein to or beyond the periplasmic space. Secondly, the membranes of the bacteria have been modified by a mutational change in the bacterial DNA to be permeable to proteins.

Proteins produced using the secretory bacteria and methods of the invention have full biological activity and are believed to be in the correctly folded conformation. Therefore, the manipulations generally required to obtain biologically active recombinant proteins from *E. coli* using the methods of the prior art are eliminated.

A wide variety of *E. coli* strains can be used in this invention, including but not limited to C600, W3110, AB1157, P678, C511, HB101, MM294, JM83 and TB1. In the example below, commercially available strain MM294 was converted to a streptomycin-resistant strain designated 294S prior to mutagenesis, for reasons entirely unrelated to this invention. Strain MM294 or many of the other available *E. coli* strains, however, could have been used instead.

Mutation of the bacteria can be carried out by any of the standard methods known in the art. In the example below, ultraviolet radiation was used as the mutagenic agent, but chemical agents can be used as well. For example, N-methyl-N'-nitro-N-nitrosoguanidine can be used as described by Lopes et al., supra, or Lazzaroni et al., supra.

*E. coli* mutants suitable for use in this invention are characterized by two essential criteria—resistance to infection by bacteriophage T7 and an ability to secrete substantial amounts of a periplasmic protein into culture medium in which the mutants are grown. Analysis for resistance to infection by T7 can be conveniently carried out as described by Branes et al. [J. Bacteriol. 154:1462 (1983)] and illustrated below.

Analysis for increased permeability to periplasmic proteins can be carried out using any of the known periplasmic proteins as a marker and an appropriate readily visualized assay for the protein selected. In the example below, secretion of ribonuclease I from the periplasm was detected by observing the ability of the secreted enzyme to produce a "halo" or clear zone in agar containing yeast RNA. If an ampicillin-resistant *E. coli* strain is used, an assay for secreted β-lactamase can be carried out as described by Zinder et al., supra, etc.

Numerous heterologous proteins can be produced by the methods of this invention. Although human interleukin-4 is used to illustrate the invention below, in principle any protein can be made for which a DNA sequence encoding the protein can be obtained. Such DNA sequences can readily be made, e.g., by applying standard cloning methods to make cDNA from mRNA isolated from cells known to produce the protein. Libraries constructed from such cDNA can be made and probed using standard methods.

In fact, human GM-CSF and a soluble gamma interferon receptor have also been produced using the secretory strains of this invention. Both displayed a high level of biological activity.

The methodology required has been described, e.g., by Okayama et al. [Mol. Cell. Biol. 2:161 (1982); Meth. Enzymol. 154:3 (1987)], Margolskee et al. [Mol. Cell. Biol. 8:2837 (1988)] and Gubler et al. [Gene 25:263 (1983)]. For a review of cDNA cloning methods see Kimmel et al., Meth. Enzymol. 152:307 (1987). Standard chemical synthetic methods can also be used to make the genes, if the nucleotide sequences of the genes are known.

Proteins synthesized in the cytoplasm of *E. coli* must be fused to a signal peptide at the amino terminus for transport to the periplasm. Many of the known signal peptides of the periplasmic or outer membrane proteins of *E. coli* can be used for this purpose. For example, Talmadge et al., Proc. Natl. Acad. Sci. USA 77:3369 (1980) have described the construction of a vector designated pKT287 which contains the bla gene of pBR322. The first 23 amino acids encoded by bla comprise the β-lactamase signal sequence. If a gene is inserted in frame at the Pst I site of pKT287, a fusion protein will be produced during expression which contains the signal peptide. Plasmid pKT287 is illustrated by Maniatis et al., supra, page 428.

Similarly, Silhavy has prepared a plasmid designated pMH621 which contains a gene encoding the *E. coli* ompF signal peptide, (Maniatis et al., supra, pp. 429–430). Insertion of a heterologous DNA sequence encoding a desired protein at the Bg.III site of pMH621 will produce a fusion protein containing the ompF signal peptide. In the example below, another omp signal peptide, the ompA peptide, was used.

OmpA and ompF are signal peptides for *E. coli* outer membrane proteins. The amino acid sequences of these signal peptides have been disclosed by Pollitt et al., in Bacterial Outer Membranes as Model Systems, 1987, M. Inouye (ed.), John Wiley & Sons, New York, pp. 117–139. Watson [Nucleic Acids Res. 12:5145 (1984)] has disclosed that the primary structures of over 277 prokaryotic and eukaryotic signal sequences are now known. Oligonucleotides having such prokaryotic signal sequences can be chemically synthesized for use in this invention using the phosphotriester or other known methods, preferably in a solid-phase system, and inserted into an appropriate expression vector.

Although differing in their amino acid sequences, bacterial signal peptides appear to have three common regions. At the amino terminus, there is a region of several hydrophilic residues which contains one or more lysine or arginine residues. Following this basic region is a central hydrophobic core containing about eight to fifteen hydrophobic residues, with Leu, Ala and Val predominating. To the carboxyl side of the hydrophobic region is a region which is cleaved during processing to produce the mature protein in the periplasm or outer membrane. Cleavage usually occurs at a site about four to eight residues from the hydrophobic region.

In the example below, the cleavage of the ompA signal peptide is such that a protein having the full amino acid sequence of mature human interleukin-4 is produced without the extraneous amino-terminal Met residue which is often added to proteins during cytoplasmic expression in E. coli.

DNA sequences encoding an E. coli signal peptide and a desired heterologous protein can be operatively linked in frame in many known vectors which are capable of antonomous replication and expression in E. coli, including but not limited to pBR322, pBR325, pUC8, pUC9, pUC18, pUC19, pAH3, pKGT269-2 and pRGT857-11. The two DNA sequences can be ligated together and then inserted into a vector, or a vector can first be prepared which contains a sequence encoding a signal peptide. Any heterologous DNA sequence can then be inserted at the signal peptide site to produce the desired fusion sequence. Preferably, three vectors are prepared encoding a signal peptide so that any given heterologous gene inserted will be in correct reading frame in one of them.

It may also be possible to utilize the natural nucleotide sequence of a heterologous gene to encode the signal peptide. For example, Talmadge et al. (Nature 294:176 (1981)) have reported that the signal sequence normally associated with proinsulin also functions in E. coli to allow the secretion of proinsulin.

Preferably, the recombinant vectors used in the invention are under the control of a regulatable promoter/operator (po) system such as the well known trp, lac or λpL promotor. Many po systems are known in the art which are under the control of thermally sensitive repressors; raising the incubation temperature releases the repression and permits controlled expression. Others can be controlled using chemical inducers (e.g., indolylacetic acid (trp) and isopropyl-β-D-thiogalactoside (IPTG, lac)).

Although specific recombinant plasmids are described below to illustrate this invention, it must be stressed that they are merely representative of the many recombinant plasmids that could be used instead.

Following construction, the recombinant vectors can be transformed into the mutant bacteria by standard methods (see, e.g., Maniatis et al., supra, page 250), and the transformants can be cloned in an appropriate medium.

Determination of whether a given transformant clone is secreting biologically active protein can be made using standard immunochemical or bioassay methods. Aliquots of culture medium into which a lymphokine such as interleukin-2 or interleukin-4 has been secreted can be assayed for T cell growth factor activity as described, e.g., by Devos et al. (Nucleic Acids Res. 11:4307 (1983)). The end points of such assays can be radioisotopic or colorimetric measurements (Mosmann, J. Immunol. Meth. 65:55 (1983)). Interferon bioassays can be carried out as described, e.g., by DeChiara et al. (U.S. Pat. No. 4,816,566), etc.

More rapid screening of secretory clones can be carried out by immunoprecipitation or enzyme-linked immunosorbent assay (ELISA). Antibodies against the desired protein can be prepared using standard methods. Monoclonal antibodies, which can readily be prepared as described by Kohler and Milstein (Nature 256:495 (1975); Eur. J. Immunol. 6:511 (1976)), are preferred.

In making monoclonal antibodies, the desired protein is used to immunize animals such as mice, rats, horses, sheep, pigs, rabbits, etc., to obtain antibody-producing somatic cells for fusion to myeloma cells.

Somatic cells with the potential to produce antibodies particularly B cells, are suitable for fusion with a myeloma cell line. These somatic cells may be derived from the lymph nodes, spleens and peripheral blood of primed animals. In the exemplary embodiment of this invention rat spleen cells are used, in part because these cells produce a relatively high percentage of stable fusions with mouse myeloma lines. It would be possible, however, to use mouse, rabbit, frog or other cells instead.

Specialized myeloma cell lines have been developed from lymphocytic tumors for use in hyridoma-producing fusion procedures (Kohler and Milstein, Eur. J. Immunol. 6:511 (1976); Shulman et al., Nature 276:269 (1978); Volk et al., J. Virol. 42:220 (1982)). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. The purpose of using monoclonal techniques is to obtain fused hybrid cell lines with unlimited lifespans that produce the desired single antibody under the genetic control of the somatic cell component of the hybridoma. To eliminate the production of tumor cell antibodies by the hybridomas, myeloma cell lines incapable of producing light or heavy immunoglobulin chains or deficient in antibody secretion mechanisms are used. A third reason for selection of these cell lines is for their suitability and efficiency for fusion.

Many myeloma cell lines may be used for the production of fused cell hybrids, including, e.g., P3X63-Ag8, P3/NS1-Ag4-1, Sp2/0-Ag14 and S194/5.XXO.Bu.1. The P3X63-Ag8 and P3/NS1-Ag4-1 cell lines have been described by Kohler and Milstein (Eur. J. Immunol. 6:511 (1976)). Shulman et al. (Nature 276:269 (1978)) developed the Sp2/0-Ag14 myeloma line. The S194/5.XXO.Bu.1 line was reported by Trowbridge (J. Exp. Med. 148:313 (1979)). In the example of the present invention, the P3X63-Ag8.653 line (ATCC CRL 1580) was used.

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described by Kohler and Milstein, supra, Gefter et al.

(Somatic Cell Genet. 3:231 (1977)), and Volk et al. (J. Virol. 42:220 (1982)). The fusion-promoting agents used by those investigators were Sendai virus and polyethylene glycol (PEG). The fusion procedure of the example of the present invention uses PEG.

Because fusion procedures produce viable hybrids at very low frequency (e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques which have been described in the literature (see, e.g., Kennet et al. (editors), Monoclonal Antibodies and Hybridomas: A New Dimension in Biological Analyses, pp. 376–384, Plenum Press, New York (1980)).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation.

Preferably, monoclonal antibodies are used which specifically bind to the correctly folded, biologically active form of the desired protein but not to denatured forms of the protein. Such antibodies can be obtained by producing a large number of hybridoma clones secreting antibodies against the protein, and then screening the media of the hybridomas with both the active and denatured protein to find hybridomas producing the desired antibodies. An inactive form of a protein can readily be prepared by treating a sample of a protein with sodium dodecylsulfate (SDS) to denature the protein.

The use of antibodies which recognize only the active protein eliminates the need for more time-consuming bioassays. Antibodies lacking such specificity, however, can be used for rapid screening. Clones found to be positive in such screening can then be assayed for bioactivity.

In a preferred embodiment, secretory clone screening is carried out with the use of a nitrocellulose membrane assembly. A first nitrocellulose membrane is brought into contact with the surface of a dispersed culture of transformants. This membrane, onto which a portion of the colonies in the culture is transferred due to the contact, is then placed directly atop a second nitrocellulose membrane in contact with a growth medium, to form the membrane assembly. The assembly is then incubated on the growth medium under conditions in which the heterologous protein secreted by the transferred mutant bacterial cells passes through the first membrane and into the second. The membranes are separated following the incubation, and the protein on the second membrane is detected using the specific antibodies which bind to the protein to form antibody-protein complexes.

After the second membrane is washed to remove unbound materials, the protein-antibody complexes can be detected using labeled second antibodies directed against the first antibodies on the membrane. For example, if the antibodies specific for the protein are murine monoclonal antibodies, labeled anti-mouse immunoglobulin antibodies will be used. These second antibodies can be labeled with a compound that fluoresces at a particular wave length such as rhodamine or, preferably, with an enzyme that catalyzes a visible chemical reaction. Various peroxidases, glucose oxidase, β-galactosidase and alkaline phosphatase are enzymes that can be used for this purpose. Through the use of the labeled second antibodies, visible foci will appear where the secreted protein is present on the membrane.

Figure 1:
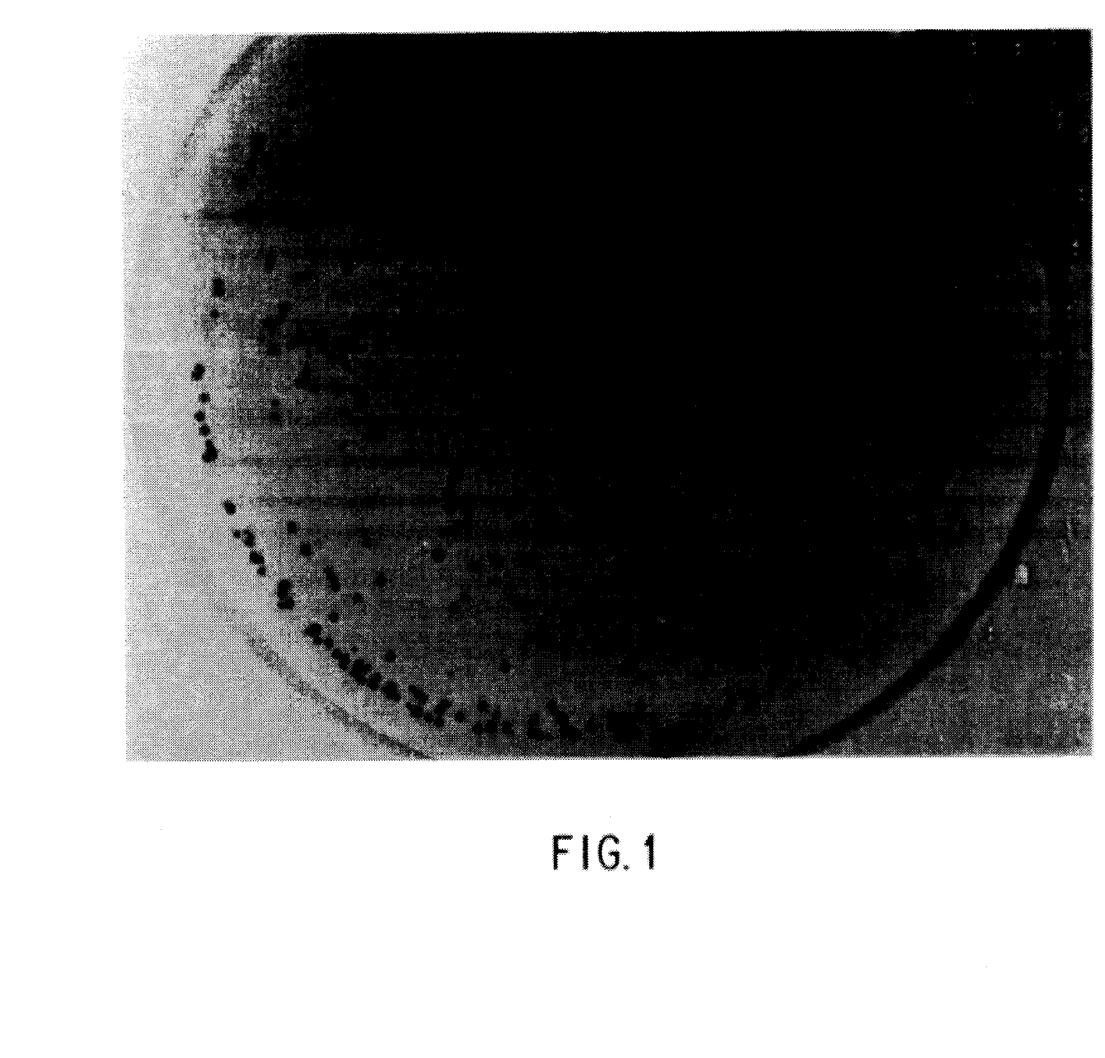
FIG. 1 a photograph of an analytical nitrocellulose membrane showing visible foci where secreted interleukin-4 was present. The interleukin-4 was visualized by first treating the membrane with polyvalent antiserum specific for the protein and then with a labeled antiserum specific for the anti-interleukin-4 antiserum. The arrowhead points to an especially intense spot representing a secretory colony that was selected for cloning and further evaluation.

A representative membrane containing such foci is shown in FIG. 1, where an arrowhead points to a more intense spot representing a colony selected for further evaluation.

After the positions of the bound protein on the second membrane are rendered visible, the culture and the second membrane are aligned so that the visible foci are superimposed with the transformant colonies secreting the protein. Secreting colonies thus identified are then removed from the culture and subcultured in an appropriate growth medium or fermentation broth.

In some instances, it may be desirable to employ a third nitrocellulose membrane in the membrane assembly. This membrane is placed between the second membrane and the growth medium so that, during the above-mentioned incubation, protein secreted by the transferred colonies will pass into both the second and third membranes. Immunochemical detection of protein foci on the third membrane as described above following separation of the membranes serves to confirm that any negative reactions observed on the second membrane are not false negatives. Preferably, the first antibodies used in analysis of the second membrane are specific for the biologically active, correctly folded form of the protein only, while the first antibodies used on the third membrane will bind to any form of the protein, whether denatured or not.

Because the exposure to the mutagenic agent might have caused mutational changes in the expression plasmid as well as in the bacterial DNA, it is preferable to "cure" the selected clones by first removing the plasmids from them and then replacing them with ones that had never been exposed to the mutagenic agent. This curing can readily be accomplished using standard methods.

For example, the plasmid can be expelled by culturing the cells in the presence of acridine orange, as described by Watanabe et al. (J. Bacteriol. 81:679 (1961)). Another method is to simply culture the cells in the absence of the selection marker used to isolate the transformants. In the example below, the transformed cells were able to grow in the presence of ampicillin only because the plasmid directed expression of an enzyme that degraded the antibiotic. With ampicillin present in the culture medium, there was selective pressure on the otherwise sensitive host cells to retain the plasmid; without ampicillin, the plasmid was unnecessary for cell survival and was thus spontaneously lost.

Although only a few secretory clones of *E. coli* are described below in detail to illustrate this invention, the methods used routinely produce substantial numbers of useful secretory mutants. From about $10^{11}$ cells exposed to the mutagenic agent, about 300–500 colonies will be produced which survive infection by T7. Of these resistant colonies, about one-third to one-half will also secrete substantial amounts of periplasmic proteins into the culture medium.

Preferably, the secretory strains of the invention are further evaluated to ensure that they are stable to prolonged culture and not leaking the desired heterologous protein because of general cellular degeneration.

To ensure that selected strains are stable, they are preferably subcultured for a number of generations and observed for evidence of degeneration such as spontaneous lysis. Proof that the desired heterologous protein is not appearing in the culture medium because the cells are simply degenerating is preferably obtained by analyzing the medium for the presence of a representative *E. coli* cytoplasmic protein. If the cells are structurally intact, substantial amounts of such proteins should of course not be present in the medium. Such analysis can be carried out for any cytoplasmic protein for which a convenient assay is available, such as glucose-6-phosphate dehydrogenase.

In many cases even more effective secreting strains can be produced by subcloning and culturing strains obtained by the foregoing methods and subjecting the cells to one or more additional rounds of mutagenesis, cloning and selection.

The identified *E. coli* secretory strains are cultured under conditions in which both the DNA sequence encoding the signal peptide and the sequence encoding the desired heterologous protein are expressed. The bacterial cells are then separated from the culture medium and the protein is isolated from the medium using standard techniques. Methods which can be used to isolate the protein include, e.g., acid or salt precipitation, ion-exchange chromatography, metal chelate chromatography, gel filtration, high performance liquid chromatography, preparative disc gel or curtain electrophoresis, isoelectric focusing, low temperature organic solvent fractionation, countercurrent distribution, and immunoaffinity chromatography.

Both the quantity and quality of the heterologous protein secretion obtained using the secretory strains and methods of this invention can be superior to the results of using the methods of the art. For example, Lundell et al. (J. Ind. Microbiol., 5:215 (1990) have fused a DNA sequence encoding an ompA signal peptide to a human interleukin-4 gene in a recombinant vector. Upon inducing expression of the DNA with IPTG in unmutated *E. coli* strain 294, Lundell et all found that about 30–50% of the processed interleukin-4 was secreted into the culture medium.

In contrast, essentially all of the processed interleukin-4 is secreted by the mutant strains of this invention into the medium. Furthermore, subsequent analysis of secreted interleukin-4 recovered from the culture medium of Lundell et al. has shown that its physicochemical and biological properties are different from those of the lymphokine made by the methods of this invention.

Firstly, the amount of interleukin-4 activity recovered from *E. coli* strain 294 was much lower than the amount obtained from an approximately equal number of cells of one of the secretory strains of this invention. Secondly, interleukin-4 produced by the Lundell et al. system was not recognized by a monoclonal antibody specific for highly active interleukin-4 (see use of antibody 11B4 below). Thirdly, interleukin-4 recovered from the medium of the Lundell et. al. system did not bind to chromatography columns which retained interleukin-4 secreted by the mutant *E. coli* strains of the present invention. The lower amount of activity and different physical properties of the interleukin-4 released by the nonmutant bacteria suggest that that protein may have been in a different, less active conformational form.

EXAMPLE

In the example that follows, percentages for solids in solid mixtures, liquids in liquids, and solids in liquids are on a wt/wt, vol/vol and wt/vol basis, respectively, unless otherwise indicated. Sterile conditions were maintained during cell culture. All O.D. wavelengths are in nanometers.

Preparation of Antibodies Against Human Interleukin-4

A male Lewis rat was immunized intraperitoneally (i.p.) with 1 ml of a human interleukin-4 solution emulsified with 1 ml of complete Freund's adjuvant (CFA). The solution contained glycosylated recombinant human interleukin-4 expressed in COS cells and having a specific activity of $2 \times 10^7$ units/mg, at a concentration of 14 µ/ml in 10 mM Tris-HCl, 0.5M NaCl, pH 7.4.

Two weeks after the initial immunization, the rat was again injected i.p. with 1 ml of the human interleukin-4 solution emulsified with 1 ml of CFA. Three months after the second injection, the rat was boosted intravenously with 1 ml of a human interleukin-4 solution containing 15 µg of protein. Four days after the booster injection the rat was sacrificed, blood was collected, and the spleen was removed for fusion.

Spleen cells were fused with mouse P3X63-Ag8.653 myeloma cells (ATCC CRL 1580), in a 1:1 ratio using PEG. The cell suspension ($3.5 \times 10^5$ cells/ml) in HAT medium was distributed into 40 96-well plates. Ten days later hybridoma supernatants were tested for their ability to bind to human interleukin-4 immobilized directly on microtiter plates (indirect ELISA), or to human interleukin-4 bound to an immobilized polyclonal IgG fraction of rabbit anti-human interleukin-4. Bound antibody was detected by peroxidase-conjugated goat anti-rat immunoglobulin following a standard protocol. Hybridomas secreting antibodies reacting with interleukin-4 were cloned by limiting dilution. IC1.11B4.6 was one such hybridoma selected by these procedures. Antibodies from IC1.11B4.6 (designated antibody 11B4) were determined to be of the $IgG_{2a}$ isotype and were found to be specific for biologically active human interleukin-4.

This specificity was established by reacting the 11B4 monoclonal antibody with the immunizing interleukin-4 and with interleukin-4 which had been subjected to denaturing SDS polyacrylamide gel electrophoresis as described by Laemmli, Nature 227:680 (1970). The antibody recognized only the former interleukin-4, and pretreatment of the lymphokine with as little as 0.04% SDS at room temperature for 5 minutes was sufficient to abolish recognition by the antibody.

The hybridoma was stored at −70° C. in culture medium with 10% DMSO (dimethylsulfoxide) and cultured using standard mammalian cell culture techniques (RPMI 1640, medium with 10% fetal bovine serum, supplemented with 1 mM glutamine and 50 mM 2-mercaptoethanol).

Polyvalent antiserum against SDS-denatured recombinant human interleukin-4 was produced by subjecting a sample of the lymphokine to SDS polyacrylamide gel electrophoresis as described above, excising the band from the gel, and immunizing a rabbit with the recovered protein using standard techniques. The interleukin-4 had been produced in an E. coli expression system as described by Kimmenade et al. (Eur. J. Biochem. 173:109 (1988)).

Construction of Plasmid DRGT857-11

The construction of the human IL-4 expression plasmids pAH3 and pKGT269-2 and plasmid pUC 19 (FIG. 2) has been described by Lundell et al. (J. Ind. Microbiology, in the press) and by Yanisch-Perron et al. (Gene 33:103 (1985)).

Small scale isolation of plasmid DNA from saturated overnight cultures was carried out according to the procedure of Maniatis et al., supra, page 368. This procedure allows the isolation of a small quantity of DNA from a bacterial culture for analytical purposes. Larger quantities of plasmid DNA were prepared as described by Maniatis, et al., supra, page 90. Specific restriction enzyme fragments derived by the cleavage of plasmid DNA were isolated by preparative electrophoresis in 0.8% Agarose. Gels were run at 150 volts for 4 hours in tris-borate buffer (Maniatis et al., supra, page 156) and then stained with ethidium bromide to visualize the DNA. Appropriate gel sections were excised and electroeluted at 150 volts for 60 minutes. The DNA was then concentrated by precipitation with 2 volumes of ethanol.

The restriction enzymes, DNA polymerase I (Klenow fragment) and T4 DNA ligase were products of New England Biolabs, Beverly, Mass., and the methods and conditions for the use of these enzymes were essentially those of the manufacturer.

T4 DNA ligation was carried out for at least 24 hours at 4° C. Klenow blunt-ending of single-stranded DNA ends was carried out in a buffer containing 10 mM Tris-HCl, pH 7.5, 2.5 mM dGTP, dATP, dCTP and TTP and 10 mM $MgCl_2$.

SDS polyacrylamide gel electrophoreisis was carried out essentially as described by Laemmli, supra. Fifteen percent Sepragels® (Integrated Separation Systems, Hyde Park, Mass.) were used, and total lysate protein was visualized by staining with Coomassie Brilliant Blue R-250 (Bio-Rad Laboratories). Interleukin-4 was visualized immunochemically using specific antibodies as described below, after transfer of the electrophoretically separated proteins to nitrocellulose sheets using a Hoefer Scientific Model TE 50 Transphor® electrophoresis unit.

Figure 2:
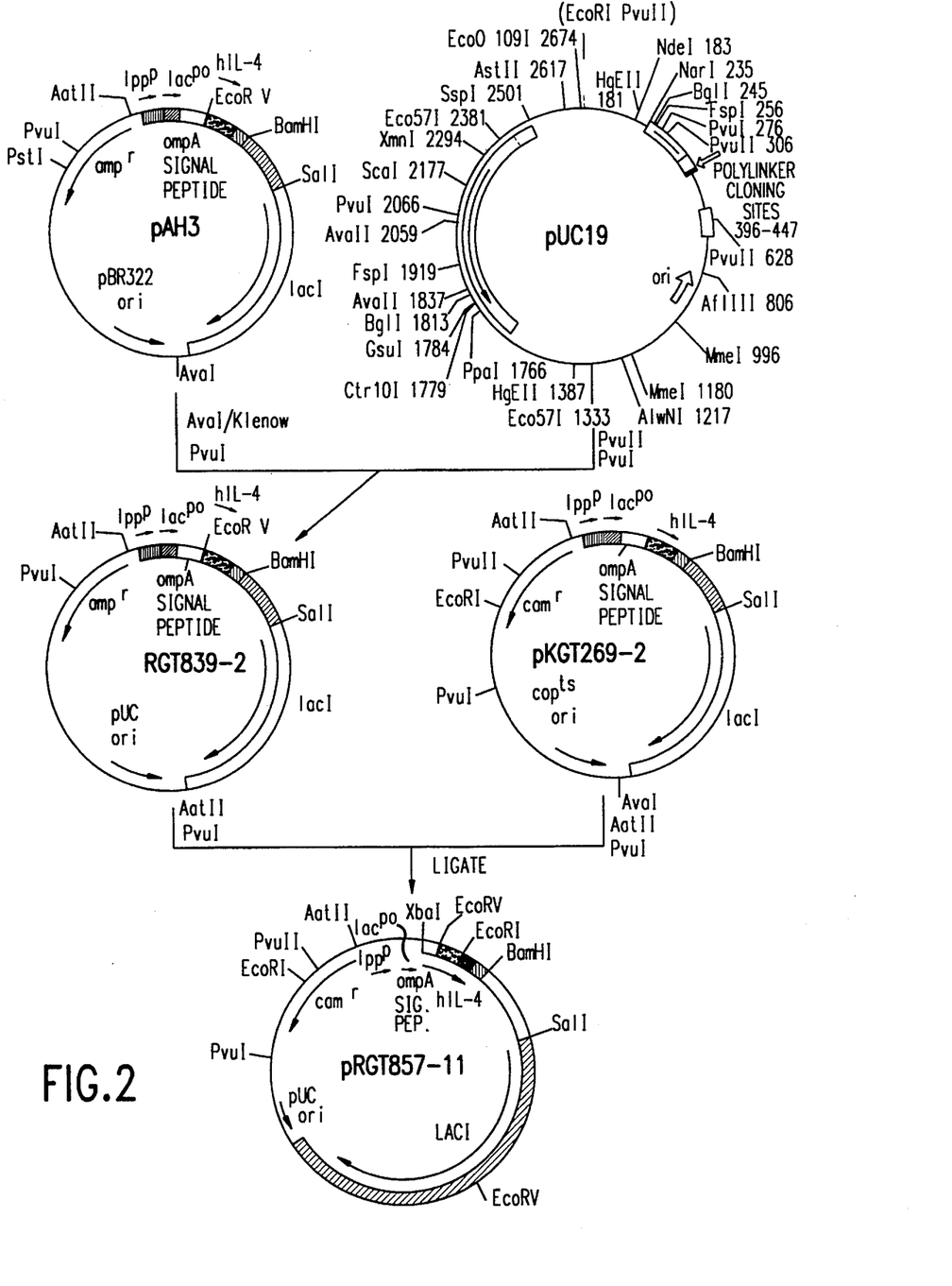
FIG. 2 is a schematic representation of the construction of plasmid pRGT857-11.

To construct pRGT857-11 used in this example, pAH3 was digested with AvaI. The 5' overhang created by this enzyme was filed in with the Klenow fragment of E. coli Polymerase I, and the DNA was digested with PvuI. A 5.8 kilobase fragment carrying the interleukin-4 and lacI regions was ligated to a 1.4 kilobase PvuII-PvuI fragment of pUC 19 carrying the pUC origin of replication. Following transformation of E. coli 294, an ampicillin-resistant interleukin-4 expression plasmid carrying the pUC origin of replication designated pRGT839-2 was isolated (FIG. 2).

Plasmids pRGT839-2 and pKGT269-2 were then both digested with AatII and PvuI. A 6.7 kilobase fragment of pRGT839-2 carrying the IL-4 and lacI regions was ligated to a 1 kilobase fragment from pKGT269-2 encoding chloramphenicol resistance. The ligation mixture was used directly to transform E. coli 294. A transformant containing plasmid pRGT857-11 was isolated.

Preparation and Selection of E. Coli Secretory Strains

A TYE broth (20 g/l Bactotryptone (Difco), 10 g/l Bacto Yeast Extract (Difco) and 5 g/l NaCl) was used for routine culturing of the bacterial strains, plating experiments and some fermentations. Most fermentations were carried out in modified GC medium (20 g/l glycerol, 30 g/l casamino acids (Difco), 30 g/l yeast extract (Difco), 5 g/l $KH_2PO_4$ and 1 g/l $MgSO_4 \cdot 7H_2O$) at 30° C. in baffled shake flasks. As required, ampicillin or chloramphenicol (obtained from Sigma Chemical Co., St. Louis, Mo.) were sometimes added at concentrations of 100 µg/ml and 10 µg/ml, respectively.

Stock strains were stored at −20° C. in 40% glycerol. Inoculum cultures were prepared by adding 0.1 ml of the glycerol stock into tubes containing 10 ml of TYE broth. After incubation overnight at 30° C., the cells were used to inoculate 100 ml of TYE medium in 500 ml baffled Edenmeyer shake flasks (Bellco, Vineland, N.J.) to $A_{660}=0.2$. The flasks were incubated at 30° C. with shaking at 250 rpm in a New Brunswick Controlled Environment Incubator Shaker. Upon reaching $A_{660}=1.0$, IPTG was added to 0.25 mM, and fermentation was continued for 4 or 18 hours.

Transformation of the various E. coli strains was carried out as described by Maniatis et al, supra, page 250.

A streptomycin-resistant form of E. coli designated 294S was produced by transducing strain MM294 with bacteriophage P1 cm1, clr100 (Miller, Experiments in Molecular Genetics, 1972, Cold Spring Harbor Laboratory) which had been grown on E. coli PAM163 (Johnson, Gen. Res. 30:273 (1977)). E. coli strain MM294 can be obtained from the American Type Culture Collection under Accession No. ATCC 33625.

E. coli 294S was irradiated in sterile water for 40 seconds at a distance of 10 inches, using a germicidal ultraviolet lamp. This treatment produced 99.9% cell death, as determined by plating on a rich TYE broth containing Tryptone: yeast extract:sodium chloride (20:10:5). The mutated cell suspension was diluted 1:5 with the rich TYE broth to a final volume of about 50 ml and incubated for 3 hours at 37° C. in the dark with-shaking in a 250 ml flask.

To select for mutants having an altered outer membrane, wild-type bacteriophage T7 was added following the incubation at a concentration of $10^8$ plaque forming units per ml. The flask was shaken at 37° C. until cell lysis was observed (about 30 minutes), after which the T7-resistant cells were collected by centrifugation at 10,000×g for 10 minutes at 4° C. and the pellet was resuspended in 1 ml of fresh broth.

The cells were spread onto TYE [Tryptone:yeast extract-:sodium chloride (20:10:5)] agar plates and incubated at 37° C. After 24 hours, each plate contained about 30–50 colonies. These colonies were further examined for outer membrane damage. One method used was to observe any increase in ribonuclease I leakage into the medium.

Single colonies of T7 bacteriophage-resistant clones were streaked across fresh TYE agar plates that had been overlaid with 4 ml of TYE agar containing 1% yeast RNA (Sigma Chemical) at pH 7. After overnight incubation at 37° C., the plates were flooded with 1N HCl. Halo size was used to determine strains leaking ribonuclease activity into the medium (Weigand et al., J. Bacteriol. 125:340 (1976)).

Another indicator of outer membrane damage in *E. coli* is failure to grow on MacConkey agar (Hancock, Ann. Rev. Microbiol. 38:237 (1984)). Two of about thirty T7-resistant colonies shown to be particularly sensitive to MacConkey agar and able to release substantial amounts of periplasmic ribonuclease I were isolated and designated RL7 and RZ21.

*E. coli* RL7 and RZ21 were transformed with plasmid pAH3 (FIG. 2) to produce strains RZ21/pAH3 and RL7/pAH3. Plasmid pAH3 produces a signal peptide which directs the transport of interleukin-4 across the inner cell membrane into the periplasm. Both transformants were fermented in the modified GC medium. Spent media from both transformants were screened for leakiness by Western blot analysis using rabbit polyclonal antiserum against human interleukin-4.

To produce strains secreting greater quantities of interleukin-4, RL7/pAH3 and RZ21/pAH3 were mutated as before with ultraviolet radiation. After growth in the dark for at least 2 hours, the irradiated cells were plated on TYE agar plates supplemented with ampicillin (100 µg/ml) and incubated overnight at 30° C. The colonies were screened by the two-membrane immunoassay (using the polyclonal antiserum) for increased release of interleukin-4, as indicated by a more intense color development under the secretory colonies.

The mutated cells were diluted and spread (0.1 ml per plate) onto TYE agar plates (142 mm diameter) containing 100 µg/ml ampicillin. After incubation at 30° C. overnight, the plates contained about 500–2000 colonies of approximately 1 mm diameter. The plates were then covered with a 137 mm nitrocellulose disc (Schleicher and Schuell) with 0.45µ pore size. The disc was gently applied from one edge to allow gradual and even wetting. The disc was immediately peeled back in one motion so that a portion of the colonies was lifted from the agar plate onto the nitrocellulose disc. The disc was placed atop another nitrocellulose disc which had previously been placed onto the surface of a sterile agar plate. The discs were then incubated overnight at 30° C.

After the incubation, the bottom disc was separated from the colony-bearing disc. The filters were incubated in 10 mM tris, pH 8, 150 mM NaCl and 0.05% (v/v) Tween-20 (polyoxyethylenesorbitan monolaurate; Bio-Rad, enzyme immunoassay purity) (TBST) containing 1% BSA (bovine serum albumin) at room temperature for 60 minutes. The filters were then incubated with a first antibody which was either rabbit polyclonal antiserum (1:1500 dilution in TBST/BSA; used for determination of total interleukin-4) or monoclonal antiserum (antibody 11B4) (1:10 dilution of hybridoma culture supernatant in TBST/BSA; used for determination of interleukin-4 in its native conformation) at room temperature for 30 minutes.

The filters were washed three times in TBST and incubated with an alkaline phosphatase-linked second antibody specific for the first antibody used, for 30 minutes. The filters were washed three times with TBST and stained with an alkaline phosphatase substrate (ProtoBlot System of Promega Biotec). Visible foci which appeared were then aligned with the original plates, and colonies showing increased human interleukin-4-specific staining were selected.

The selected colonies were cured of the plasmid by continuous transfer in non-selective (ampicillin deficient) media, followed by streaking on non-selective TYE plates. Colonies scoring negative for growth on ampicillin plates were checked for the absence of plasmids and then retransformed with pAH3.

RL7 and RZ21 derived clones harboring pAH3 were cultured in TYE with 100 µg/ml ampicillin. These clones were screened for increased release of the lymphokine by dot immunoblotting whole broths obtained from 10-ml tube fermentations. Colonies were evaluated as above using the 11B4 monoclonal antibody to human interleukin-4 and alkaline phosphatase-conjugated goat anti-rat IgG.

One strain produced by the further mutation of RL7 and selected as a high producing Strain was designated RL731. Two improved strains derived in like fashion from RZ21 were designated RS631 and RL2117.

Figure 3:
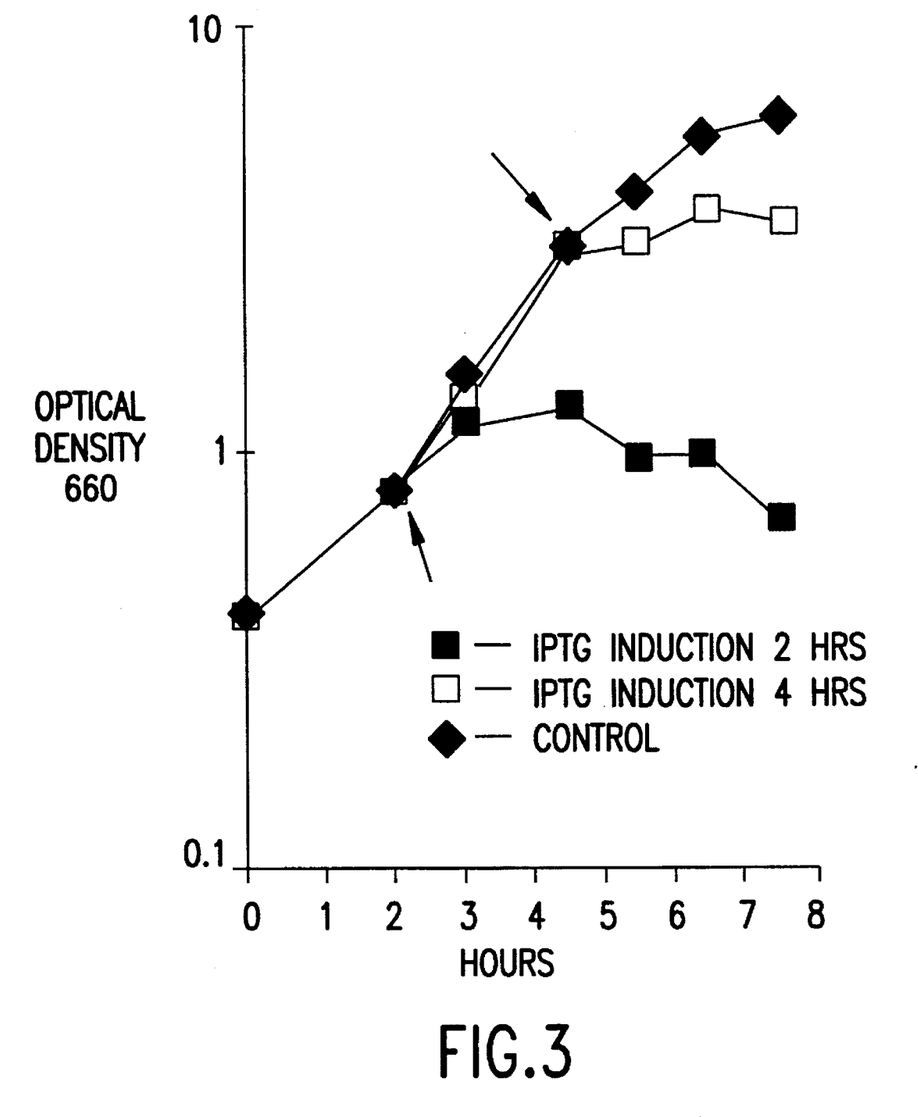
FIG. 3 is a graphical representation of the growth of *E. coli* RL731/pRGT857-11, showing cell growth (O.D.$_{.660}$) as a function of time. The cells were grown in TYE medium at 30° C. and then left uninduced (closed diamonds) or induced with 1 mM IPTG at 2 hours (closed squares) or 4 hours (open squares) from the initiation of culturing. IPTG induction caused an almost immediate cessation of further growth.

*E. coli* RL731 did not grow when induced by IPTG (FIG. 3). To modify RL731 for growth in the presence of IPTG, the strain harboring plasmid pRGT857-11 was mutated with ultraviolet light as before. After growth in the dark as above, the cells were plated on TYE agar supplemented with 10 µg/ml chloramphenicol and 1 mM IPTG (isopropyl β-D thiogalactoside).

Figure 4:
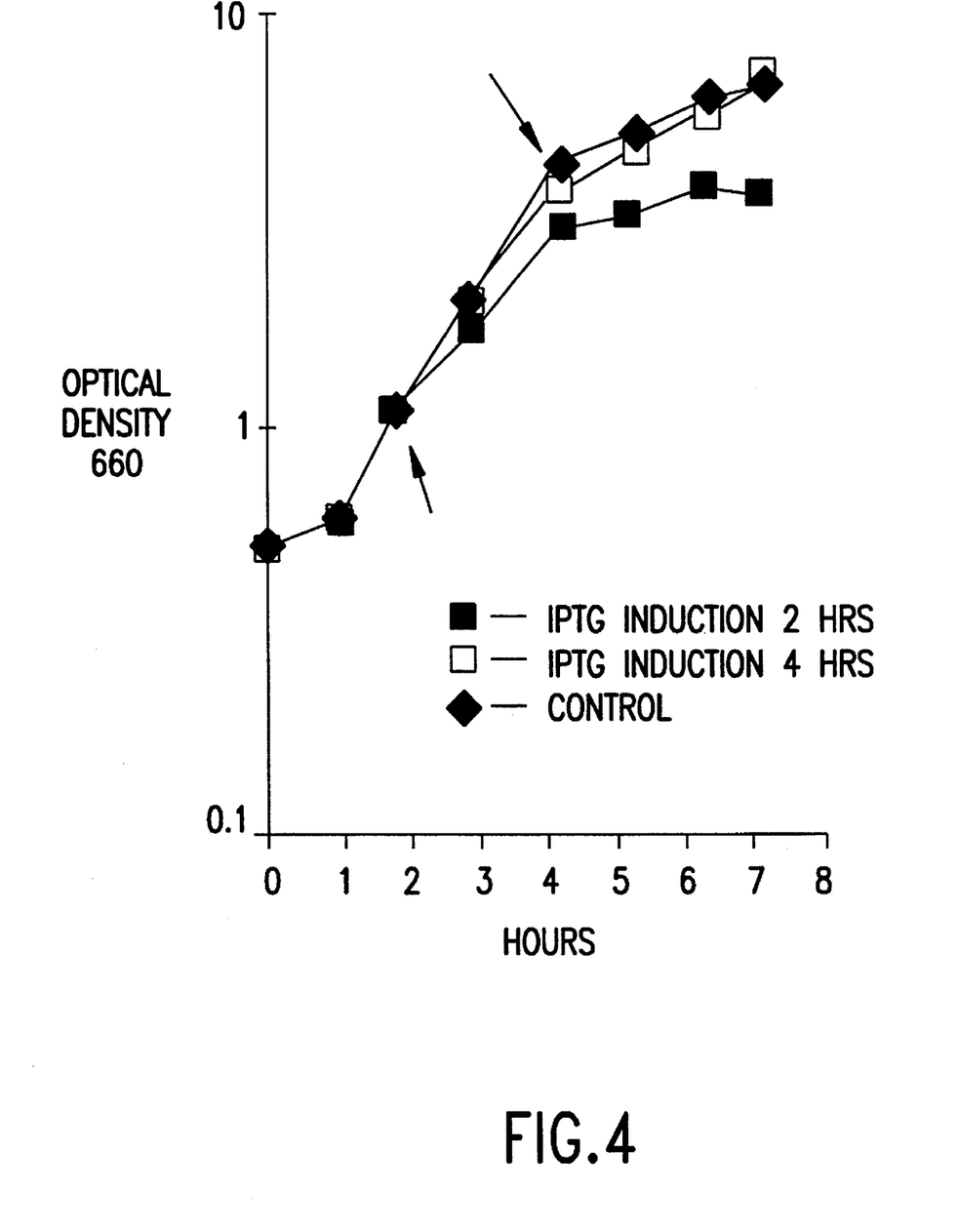
FIG. 4 is a graphical representation of the growth of *E. coli* RL7321/pRGT857-11, showing cell growth (O.D.$_{.660}$) as a function of time. The cells were grown with or without IPTG induction as described in the legend to FIG. 3. Cell growth was essentially unaffected by the presence of the inducer.

The cells were plated at a density of about $10^4$ colony forming units per ml. About 5–10 colonies per plate developed upon overnight incubation. Over 75 colonies were purified by streaking and checked for interleukin-4 production by Western blot analysis. Clones that showed the heaviest bands were cured of their plasmids as before, retransformed with pRGT857-11 and checked for retention of the ability to secrete high levels of interleukin-4. One strain picked for most satisfactory characteristics, including production and leakage of biologically active human interleukin-4 and continued cell growth after the induction of expression by IPTG was designated RL732I. The growth characteristics of strain RL732I following IPTG induction are shown in FIG. 4.

Comparison of Human Interleukin-4 Production by Unmutated and Singly- and Doubly mutated *E. coli*

To demonstrate the enhanced secretory ability of the strains of this invention and the effect of repeated mutagenesis and selection, cultures of unmutated strain 294S and singly- (strain RZ21) and doubly-mutated (strain RS631) *E. coli* harboring plasmid pAH3 were fermented as described above in 20:10:5 TYE medium. Expression was then induced by the addition of 1 mM IPTG. Six hours post induction, the amount of interleukin-4 released by incubation of a 10× cell concentration of the various transformants in 20:10:5 TYE medium containing 2 mM EDTA for 1 hour at 37° C. was determined. The interleukin-4 in the medium was assayed by the method of Yokota, et al., Proc. Natl. Acad. Sci. USA 83:5894 (1986), with the results shown in Table 1.

TABLE 1

Interleukin-4 Production

| E. coli Strain | Bioactivity* (Units/ml) |
|---|---|
| 294S/pAH3 | 2,005 |
| RZ21/pAH3 | 21,798 |
| RS631/pAH3 | 97,010 |

*Activity values are corrected to an $O.D._{660}$ of 30.0, so that secretion by equal numbers of cells is compared. One microgram of pure human interleukin-4 has about 20,000 units of activity in the assay used.

The data of Table 1 show that singly-mutated secretory strain RZ21 produced more than 10 times the amount of interleukin-4 in the medium than unmutated strain 294S. Doubly-mutated strain RS631 in turn produced almost five times more activity in the medium than did strain RZ21.

RL7 derived clones harboring pAH3 and pRGT857-11 were fermented as described above. The interleukin-4 secreted directly into the medium was sampled four hours post induction with IPTG and subjected directly (without prior concentration and EDTA treatment of the cells) to bioassay as above, with the results shown in Table 2.

TABLE 2

Interleukin-4 Production

| E. coli Strain | Bioactivity[a] (Units/ml) |
|---|---|
| RL7/pAH3 | 387[b] |
| RL731/pAH3 | 1,871[b] |
| RL731/pRGT857-11 | 5,435[c] |
| RL732I/pRGT857-11 | 34,870[c] |

[a] One microgram of pure human interleukin-4 has about 20,000 units of activity in the assay used.
[b] Activity values are corrected to an $O.D._{660}$ of 1.0.
[c] Activity values are from equal batches unadjusted for cell concentration.

In Table 2, the bioactivity data for RL7/pAH3 and RL731/pAH3 are adjusted to equal numbers of cells. Therefore, it is clear that RL731/pAH3 produced about 6 times more interleukin-4 that RL7/pAH3 on a per cell basis. The data for RL731/pRGT857-11 and RL732I/pRGT857-11 were based upon equal batches unadjusted for cell concentration. Thus, the data obtained with these strains cannot be directly compared with the results from the pAH3 bearing strains. Nevertheless, it is clear that under the fermentation conditions employed, RL732I/pRGT857-11 produced about 7 times more interleukin-4 activity in the medium that did RL731/pRGT857-11. This enhanced production was due to the fact that RL732I/pRGT857-11 grew to much higher cell densities in the presence of IPTG (see FIGS. 3 and 4), although both strains produced about the same amount of interleukin-4 on a per cell basis.

Culture Deposits

Mutant E. coli strains RZ21, RL2117, RS631, RL7, RL731 and RL732I have been deposited with the American Type Culture Collection (ATCC) and assigned accession Nos. ATCC 53951, 53952, 53953, 53954, 53955 and 53956, respectively. E coli strain 294S haboring plasmids pAH3 and pKGT269-2 has been deposited with the ATCC and assigned accession Nos. ATCC 68136 and 68137, respectively. Hybridoma IC1.11B4.6 producing monoclonal antibody 11B4 has been deposited with the ATCC and assigned accession No. ATCC HB 9809. All of these deposits have been made under the provisions of the Budapest Treaty on the International Recognition of the Deposit of Microorganisms for the Purposes of Patent Procedures.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. An *Escherichia coli* bacterium capable of secreting a heterologous gene product into the culture medium, comprising:

(a) a mutant *E. coli* bacterium characterized by resistance to infection by bacteriophage T7 and an ability to survive transformation with a DNA comprising a sequence encoding for a heterologous protein, and (b) a recombinant vector comprising a first DNA sequence coding for a signal peptide capable of mediating transport of a protein to the periplasmic space operatively linked to a second DNA sequence coding for a desired heterologous protein, which bacterium is capable of expressing both DNA sequences.

2. The bacterium of claim 1, wherein the bacterium is derived from a bacteriophage T7 sensitive parent cell and the bacterium is characterized by an ability to secrete at least about ten times more periplasmic proteins into the culture medium than a parent cell lacking such resistance from which the bacterium was derived.

3. The bacterium of claim 2 in which the heterologous gene product secreted is biologically active.

4. The bacterium of claim 3 in which the first DNA sequence codes for an ompA signal peptide.

5. The bacterium of claim 3 in which the second DNA sequence codes for human interleukin-4.

6. The bacterium of claim 3 in which expression of both DNA sequences is under the control of an inducible promoter.

7. The bacterium of claim 6 in which the inducible promoter is a lac promoter.

8. The bacterium of claim 5 in which the recombinant vector is plasmid pRGT857-11.

9. A method for producing a desired heterologous protein comprising:

(a) culturing an *E. coli* bacterium capable of secreting a heterologous protein into the culture medium, comprising (i) a mutant *E. coli* bacterium characterized by resistance to infection by bacteriophage T7 and an ability to survive transformation with a DNA comprising a sequence encoding for a heterologous protein, and (ii) a recombinant vector comprising a first DNA sequence coding for a signal peptide capable of mediating transport of a protein to the periplasmic space operatively linked to second DNA sequence coding for a desired heterologous protein, under conditions in which the bacterium expresses both DNA sequences and secretes the heterologous protein into the culture medium; and (b) isolating the secreted protein from the culture medium.

10. The method of claim 7, wherein the bacterium is derived from a bacteriophage T7 sensitive parent cell and the bacterium is characterized by an ability to secrete at least about ten times more periplasmic proteins into the culture medium than a parent cell lacking such resistance from which the bacterium was derived.

11. The method of claim 10 in which the heterologous gene product secreted is biologically active.

12. The method of claim 11 in which the first DNA sequence codes for an ompA signal peptide.

13. The method of claim 11 in which the second DNA sequence codes for human interleukin-4.

14. The method of claim 11 in which expression of both DNA sequences is under the control of an inducible promoter.

15. The method of claim 14 in which the inducible promoter is a lac promoter.

16. The method of claim 9 in which the bacterium is strain RZ21, RS631, RL2117, RL7, RL731 or RL732I.

17. The method of claim 13 in which the recombinant vector is plasmid pRGT857-11.

18. A method for producing and identifying an *E. coli* bacterium capable of secreting a heterologous gene product into the culture medium, comprising:

(a) subjecting *E. coli* bacteria to a sufficient amount of a mutagenic agent to produce mutational changes in the DNA of the bacteria;

(b) selecting clones of the mutants produced in step (a) for resistance to infection by bacteriophage T7 and an ability to secrete substantial amounts of periplasmic proteins into the culture medium;

(c) transforming one or more of the clones selected in step (b) with a recombinant vector comprising a first DNA sequence coding for a signal peptide capable of mediating transport of a protein to the periplasmic space operatively linked to a second DNA sequence coding for a desired heterologous protein, which recombinant vector is capable of directing expression of both DNA sequences in the bacteria; and (d) analyzing the transformed clones to determine which clones are secreting the heterologous protein.

19. The method of claim 18 in which analysis of the transformed clones is carried out by a method comprising:

(a) contacting a first nitrocellulose membrane with a dispersed culture of the transformed bacteria slated onto agar, under conditions in which a portion of colonies in the culture is transferred onto one side of the membrane;

(b) contacting the other side of the membrane of step (a) with a second nitrocellulose membrane in contact with a growth medium, to produce a membrane assembly;

(c) incubating the membrane assembly under conditions in which biologically active protein secreted by the transferred bacteria passes through the first membrane to the second membrane;

(d) separating the membranes and contacting the second membrane of step (c) with a first antibody specific for the protein, under conditions in which specific antibody-protein complexes form;

(e) washing the second membrane of step (d) to remove unbound materials;

(f) contacting the washed membrane with a labeled second antibody specific for the first antibody, under conditions in which a visible reaction occurs where first antibody-protein complexes are present on the membrane, to produce visible foci; and (g) aligning the visible foci with the bacterial colonies in the culture, thereby identifying bacteria secreting the protein.

20. The method of claim 18 in which the identified bacterial colonies are isolated from the culture.

21. The method of claim 18 in which the heterologous protein is recombinant human interleukin-4.

22. The method of claim 18 in which the mutagenic agent is ultraviolet radiation.

23. The method of claim 19 in which the membrane assembly further comprises a third nitrocellulose membrane between the second membrane and the growth medium, on which protein secreted by the bacterial colonies is detected as in steps (d) through (f).

24. The method of claim 19 in which the first antibody specifically binds to the biologically active protein but not to denatured forms of the protein.

25. The method of claim 18 which further comprises (a) culturing the transformed bacteria in a medium which causes expulsion of the recombinant vector, and (b) retransforming the bacteria with the same recombinant vector which has not been exposed to the mutagenic agent.

26. The method of claim 18, wherein the bacterium is derived from a bacteriophage T7 sensitive parent cell and the clones of step (b) secrete at least about ten times more periplasmic proteins into the culture medium than parent cells lacking such resistance from which the clones were derived.

27. The method of claim 26 in which the heterologous gene product secreted is biologically active.

28. An *E. coli* bacterium selected from the group consisting of RZ21, RS631, RL2117, RL7, RL731 and RL732I.

* * * * *